US00PP29814P2

(12) United States Plant Patent
O'Connell

(10) Patent No.: US PP29,814 P2
(45) Date of Patent: Nov. 6, 2018

(54) ***ECHEVERIA* 'SEA DRAGON'**

(50) Latin Name: ***Echeveria* hybrid**
Varietal Denomination: Sea Dragon

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/732,296

(22) Filed: Oct. 19, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Echeveria* cultivar named 'Sea Dragon' is disclosed, characterized by rosettes comprised of wide aqua colored leaves with a single large carnunculation. Leaf margins are highly anfratuous and colored rose pink. Foliage shape is spatulate with a large distinctively orbicular upper section. The new variety is an *Echeveria*, part of the Crassulaceae complex that includes *Aeonium, Crassula, Graptopetalum, Pachyphytum, Sedum* and others. *Echeveria* is a popular genus, typically produced as container plants for the patio or as landscape plants, as a variety of ornamental purposes.

1 Drawing Sheet

Latin name of the genus and species: *Echeveria* hybrid. Variety denomination: 'SEA DRAGON'.

BACKGROUND OF THE INVENTION

The new cultivar, *Echeveria* 'Sea Dragon', is the product of a planned breeding program. The new variety originated from a cross pollination of the proprietary, unpatented, seed parent, *Echeveria* 'GG3' with the pollen parent an unpatented, proprietary variety of *Echeveria* referred to as '21'. The cross pollination was made during June, 2012 in Vista, Calif., at a commercial greenhouse. The new cultivar 'Sea Dragon' was discovered by the inventor, Renee O' Connell, in August, 2013, in Vista, Calif. at a commercial greenhouse.

Asexual reproduction of the new cultivar 'Sea Dragon' was first performed in Vista, Calif., at a commercial greenhouse, by terminal vegetative cuttings in August, 2013. *Echeveria* 'Sea Dragon' has since produced multiple generations and has shown that the unique features of this cultivar are stable and reproduced true to type.

SUMMARY OF THE INVENTION

The cultivar 'Sea Dragon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SEA DRAGON'. These characteristics in combination distinguish 'SEA DRAGON' as a new and distinct *Echeveria* cultivar:

1. Rosettes comprised of wide aqua colored leaves with carunculations.
2. Anfractuous leaf margins colored rose pink.

3. Foliage that is more rounded and wider than many comparable carunculated *Echeveria* hybrids, which often produce longer, narrower leaves.
4. The new cultivar *Echeveria* 'Sea Dragon' produces wider, rounder aqua leaves with centered carunculations, attractively accented by very anfractuous leaf margins in contrasting rose pink, a combination not seen in other comparable *Echeverias*.

PARENTAL COMPARISON

Plants of the new cultivar are similar to plants of the seed parent, most horticultural characteristics, however, plants of the new cultivar differ in the following;

1. *Echeveria* 'Sea Dragon' displays leaves with very anfractuous margins, whereas the leaves of *Echeveria* 'GG3' show very little crenations along margins.
2. *Echeveria* 'Sea Dragon' displays rounder, wider obovate leaves whereas *Echeveria* 'GG3' produces leaves that are longer and narrower.
3. *Echeveria* 'Sea Dragon' produces leaves that are aqua, whereas the leaves of *Echeveria* 'GG3' display violet gray tints.
4. *Echeveria* 'Sea Dragon' displays less anfractuity than does *Echeveria* 'GG3'.
5. The anfractuous margins of *Echeveria* 'Sea Dragon' are rose pink, contrasting an aqua leaf, whereas the anfractuous margins of *Echeveria* 'GG3' are very close in color to the leaf color, thereby not providing the attractive contrast.

Plants of the new cultivar are similar to plants of the pollen parent, most horticultural characteristics, however, plants of the new cultivar differ in the following;

1. Leaves of *Echeveria* 'Sea Dragon' are blue-green with a single large, round, centered carunculation, whereas leaves of *Echeveria* '21' are silvery blue with a long ovate, less centered carunculation.

2. *Echeveria* 'Sea Dragon', displays very anfractuous margins in a contrasting rose-pink color, whereas *Echeveria* '21' displays only an occasional incidence of anfractuity in the leaf margin, and there is no contrasting marginal color.
3. The rosette of *Echeveria* 'Sea Dragon' typically grows larger than that of *Echeveria* '21'.

COMMERCIAL COMPARISON

The new cultivar 'Sea Dragon' can be compared to the unpatented commercial variety *Echeveria* 'Barbillion'. Plants of the *Echeveria* 'Barbillion' are similar to plants of the new cultivar 'Sea Dragon' in most horticultural characteristics. However, the new cultivar 'Sea Dragon' differs in the following:

1. *Echeveria* 'Sea Dragon' displays very anfractuous margins, whereas *Echeveria* 'Barbillion' produces a margin that is nearly devoid of crenations.
2. *Echeveria* 'Sea Dragon' produces pink margins, contrasting with the leaf blade color margin coloration of 'Barbillon' is similar to the leaf blade color
3. *Echeveria* 'Sea Dragon' produces a wider obovate-orbiculate leaf with centrally placed carunculation, as compared with the longer, narrower leaf, with long carunculation produced by *Echeveria* 'Barbillion'.
4. *Echeveria* 'Sea Dragon' is faster growing than *Echeveria* 'Barbillion'.

The new cultivar 'Sea Dragon' can be compared to the unpatented commercial variety *Echeveria* 'Cameo'. Plants of *Echeveria* 'Cameo' are similar to plants of the new cultivar 'Sea Dragon' in most horticultural characteristics. However, plants of the new cultivar 'Sea Dragon' differ in the following:

1. *Echeveria* 'Sea Dragon' forms leaves with very anfractuous margins, whereas the leaves of *Echeveria* 'Cameo' are devoid of anfractuity.
2. *Echeveria* 'Sea Dragon' produces leaves wider obovate-orbiculate, with a centrally placed carunculation, whereas the leaves of *Echeveria* 'Cameo' are longer and narrower.
3. The overall morphology of *Echeveria* 'Sea Dragon' is shorter than that of *Echeveria* 'Cameo', which tends to bolt.

BRIEF DESCRIPTION OF THE PHOTOGRAPH

The accompanying photographs illustrates in full color a typical plant of 'SEA DRAGON' grown in a greenhouse in Vista, Calif. Age of the plant is approximately 5 months in an 8 inch container. The photograph was taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The plant was grown under natural light conditions of 2500-4000 foot-candles. Temperatures ranged from −1° C. to 29° C. night and day. No artificial light, photoperiodic treatments or chemical treatments were given.

DETAILED BOTANICAL DESCRIPTION

In the following description, color references are made to The Royal Horticultural Society Colour Chart, 2007, except where general terms of ordinary dictionary significance are used. The following observations and measurements describe 'Sea Dragon' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria hybrid* 'SEA DRAGON'.

PROPAGATION

Type of propagation typically used: Terminal vegetative cuttings.

Time to initiate roots: About 11 days at approximately 24° C.

Root description: Fibrous.

PLANT

Age of plant described: Approximately 6 months from a cutting.

Container size of the plant described: 8 inch.

Growth habit: Upright rosulate plant.

Height: Approximately 15 to 17 cm.

Plant spread: Approximately 30 cm.

Growth rate: Moderate.

Branching characteristics: Not typically observed.

FOLIAGE

Leaf:

*Arrangement*.—Rosulate.

*Average length*.—Outermost foliage 12 to 15 cm. Inner foliage 6 to 10 cm.

*Average width*.—5 to 8 cm.

*Width at base*.—Average 2.5 cm.

*Aspect of leaf*.—Leaf folds downward, so extremely it is almost completed folded in half. Apical margin extremely undulate. One large caruncle per leaf, occurring towards apex, consuming about 30% of leaf surface.

*Shape of blade*.—Overall spatulate with large orbicular upper section.

*Apex*.—Deeply undulating crenate.

*Base*.—Broad attenuate.

*Margin*.—Anfractuous. Upper ⅓ irregularly crenate with deep undulation. Entire along lower ⅔.

*Texture of top surface*.—Glabrous, with single large caruncle.

*Texture of bottom surface*.—Glabrous.

*Appearance of top surface*.—Matte.

*Appearance of bottom surface*.—Matte.

*Quantity of leaves per plant*.—Average range 15 to 30.

Color:

*Young foliage upper side*.—Near RHS Greyed-Green 191C. Apical margin coloration near Red 41B, slightly flushed Orange-Red 35B along margin. Caruncle Grey-Green 190D with light irregular flushing near Red 41B.

*Young foliage under side*.—Near RHS Greyed-Green 191C. Apical margin coloration near Orange-Red 35B. Apex slightly flushed Greyed-Purple N187C. Center blotch near Green 138C.

*Mature foliage upper side*.—Near RHS Green 138C. Apical margin coloration near Red 44C, slightly flushed Red 44D along margin. Caruncle Grey-Green 190D with light irregular flushing near Red 41B.

*Mature foliage, under side*.—Near RHS Greyed-Green 191C. Apical margin coloration near Orange-Red 35B. Apex slightly flushed Greyed-Purple N187C. Center blotch near Green 138C.

FLOWER

Flowering: Not Observed.

REPRODUCTIVE ORGANS

Not observed.

OTHER CHARACTERISTICS

Temperature tolerance: Tolerates temperatures from approximately −2° C. to at least 35° C.

Disease/pest resistance: Neither resistance or susceptibility to normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'SEA DRAGON' as herein illustrated and described.

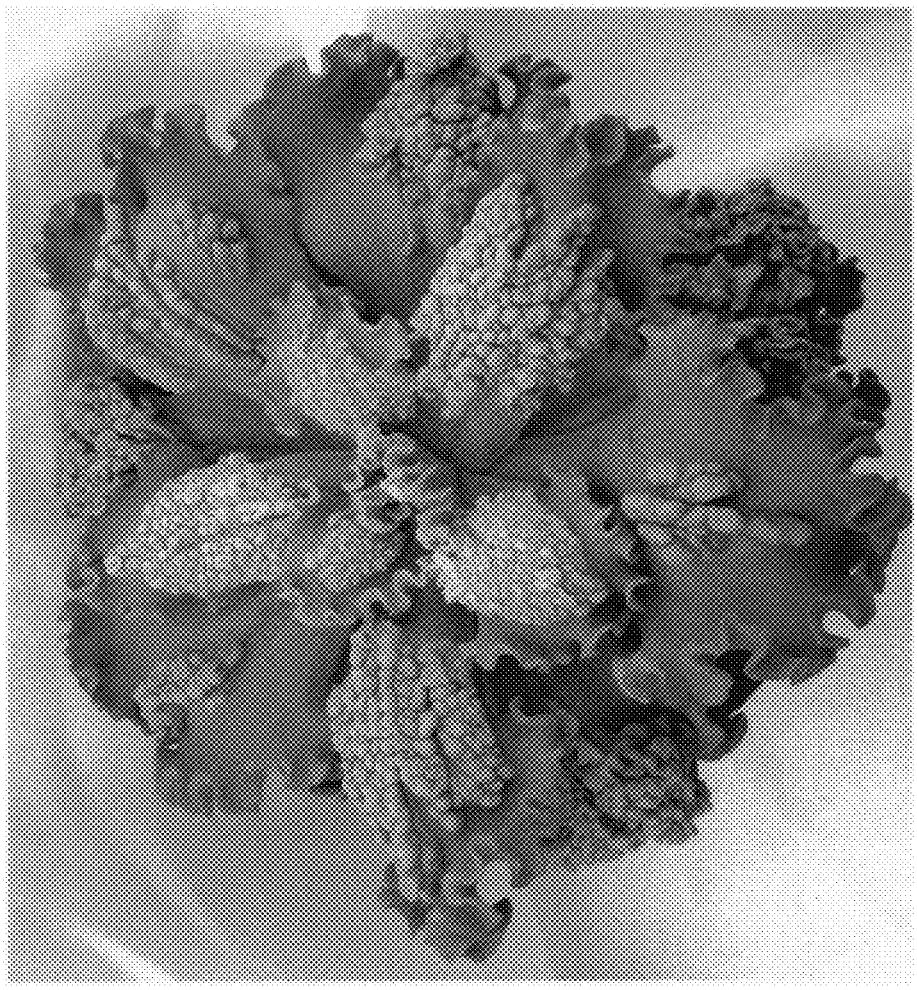

* * * * *